(12) United States Patent
Eberle et al.

(10) Patent No.: US 8,050,489 B2
(45) Date of Patent: Nov. 1, 2011

(54) AUTORADIOGRAPHY-BASED DIFFERENTIAL WEAR MAPPING

(75) Inventors: Douglas C. Eberle, San Antonio, TX (US); Craig M. Wall, San Antonio, TX (US); Martin B. Treuhaft, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 1137 days.

(21) Appl. No.: 11/781,046

(22) Filed: Jul. 20, 2007

(65) Prior Publication Data

US 2008/0019582 A1    Jan. 24, 2008

Related U.S. Application Data

(60) Provisional application No. 60/832,687, filed on Jul. 21, 2006.

(51) Int. Cl.
*G06K 9/00* (2006.01)
(52) U.S. Cl. .................. 382/149; 250/582; 250/583
(58) Field of Classification Search ............ 382/128, 382/131, 132; 250/582, 583
See application file for complete search history.

(56) References Cited

U.S. PATENT DOCUMENTS

| | | | |
|---|---|---|---|
| 3,030,442 A | 4/1962 | Brandle et al. | |
| 3,178,576 A | 4/1965 | Arvanetakis | |
| 3,521,059 A | 7/1970 | Stolle | |
| 3,769,511 A | 10/1973 | Delacy | |
| 3,992,627 A | 11/1976 | Stewart | |
| 4,692,936 A | 9/1987 | Billeaudeaux | |
| 4,694,479 A | 9/1987 | Bacskai et al. | |
| 4,924,481 A | 5/1990 | Vaughn | |
| 5,113,422 A | 5/1992 | Pinder | |
| 5,428,658 A * | 6/1995 | Oettinger et al. | 378/119 |
| 5,475,225 A * | 12/1995 | Stettner | 250/370.11 |
| 5,610,966 A | 3/1997 | Martell et al. | |
| 6,240,160 B1 | 5/2001 | Daaland et al. | |
| 6,600,806 B1 * | 7/2003 | Istar | 378/59 |

* cited by examiner

*Primary Examiner* — Claire X Wang (74) *Attorney, Agent, or Firm* — Kammer Browning PLLC (57) ABSTRACT

Methods and systems for the differential wear mapping of the surface of an object are described. The process involves establishing a radioactive wearing surface on the object through surface layer activation (SLA) and/or radioactive ion implantation (RII) and imaging the wearing surface with conformal photographic or x-ray film to produce a first autoradiograph providing a baseline profile of the wearing surface. After subjecting the object to wear during testing the wearing surface is again imaged with conformal photographic or x-ray film to produce a second autoradiograph providing a worn profile. The first and second autoradiographs of the wearing surface are digitized and compared to produce a differential wear map of the surface of the object.

20 Claims, 5 Drawing Sheets

AUTORADIOGRAPHY-BASED DIFFERENTIAL WEAR MAPPING

CROSS REFERENCE TO RELATED APPLICATIONS

This application claims the benefit under Title 35 United States Code §119(e) of U.S. Provisional Application No. 60/832,687, filed Jul. 21, 2006, the full disclosure of which is incorporated herein by reference.

BACKGROUND OF THE INVENTION

1. Field of the Invention

The present invention relates generally to methods and systems for measuring wear on material surfaces. The present invention relates more specifically to methods and systems for measuring the wear on a surface utilizing contact autoradiographs of residual radiation established by surface layer activation.

2. Description of the Related Art

Efforts have been made in the past to provide systems and methods for tracking, measuring, and monitoring the degree of wear on a variety of material surfaces. Of particular interest is the degree of wear that occurs over time on surfaces that, by operation of the machinery they are associated with, encounter abrasive surfaces or other metallic surfaces with the result that over time a significant amount of wear can occur. Many such surfaces can be found on critical engine components and other elements of vehicle systems that repetitively, or periodically, move against one another in a manner that produces wear over time. Knowing the degree and pattern of wear in components like these can be critical to safety and maintenance protocols associated with the machinery and equipment the components serve. Such testing further promotes and facilitates the development of improved designs and manufacturing techniques for these mechanical structures.

A number of efforts to determine the degree of wear on a surface involve placing or depositing some measurable characteristic onto the surface that will gradually be worn away as the surface itself is worn away. In some of these systems, this deposition process involves the placement of an additional over-layer on the surface and other times it involves providing some measurable characteristic to a surface layer (or layers) of the material itself. One obvious drawback to the use of the former approach (depositing an additional layer) is the resultant change in the character of the surface over time as the deposition layer is worn away. A further drawback is the fact that this additional layer will likely change the wear characteristics of the material. Preference is given therefore to techniques that utilize the actual material that the surface is made up of already, and that instill some characteristic in the upper layers of the material which can be monitored and measured over time.

The simplest example of such a wear monitoring system would involve a material that can be modified in some visual form on the upper layer or layers of its surface. Often this takes the form of creating physical patterns in the surface layers of the material when it is manufactured such that over time the patterns are changed or become visibly exposed as the wear on the surface occurs. This procedure, however, also suffers from the fact that the surface thereby changes physical appearance and therefore its physical characteristics, which could ultimately have an effect on the manner in which the surface interacts with other surfaces that it comes in contact with.

It would therefore be preferable if a wear monitoring system did not result in a physically changed surface over time and maintained the physical surface characteristics (with the exception, of course, of the wear that occurs) and therefore does not affect the manner in which the part or component functions (again, at least not beyond the extent to which the wear itself affects the functionality of the component).

The process of instilling a material with a characteristic that resides only in a surface layer can take a number of different approaches or forms. It is possible for example to provide a color dye to a material, with coloration variation according to a depth away from the surface into the material. Some such components may for example incorporate red dyes deep within the material, with green or blue dyes residing within the upper surface layers of the material, or more simply the density of the dye may vary according to depth. As the surface is worn away, areas beneath the surface are exposed and, upon visual inspection, differences can be determined in the degree of wear over different parts of the component. Such visually inspectable systems have drawbacks in that the degree of wear generally has to be significant in order for distinctions to be made between the upper layers and lower layers of the material. In addition, many materials are simply not receptive of dyes; at least not to the extent that visual inspection might discern quantifiable information.

Autoradiography is a process whereby the radioactive properties of a material are mapped by imaging the surface of the material (typically with photographic or x-ray film, although any two-dimensional detector array will do) and measuring the radiation generated by each particular surface area component. Autoradiography refers to the process of measuring the radiation generated by the object itself (as opposed to reflected or absorbed radiation measurements) and is generally carried out in a manner that creates an image of the radiation source whereby the radiation intensity varies in different portions across the view being measured. Such systems are used, for example, to locate radiation leaks in closed systems, and other fields where low level radiation is generated by an object in a manner that requires monitoring or tracking.

SUMMARY OF THE INVENTION

The present invention provides methods and systems for the differential wear mapping of the surface of an object. The process carried out according to these methods and systems involves establishing a radioactive wearing surface on the object through surface layer activation (SLA) or radioactive ion implantation (RII) and imaging the wearing surface with conformal photographic or x-ray film to produce a first autoradiograph providing a baseline profile of the wearing surface. After subjecting the object to wear during testing or operation, the wearing surface is again imaged with conformal photographic or x-ray film to produce a second autoradiograph providing a worn profile. The first and second (and subsequent) autoradiographs of the wearing surface are digitized and compared to produce a differential wear map of the surface of the object.

In the present invention, a method is provided wherein an object such as an engine cylinder liner is surface layer activated over some or all of the wearing inner surface. This produces radioactive elements in the first several microns of the surface whose wear is being measured. A conformal photographic or x-ray film is then placed in direct contact with the activated surface and exposed to the radiation emitted for some period of time. When developed normally, an autoradiograph is obtained giving a map of the radioactivity present in the surface of the object. Typically, this map comprises variations in the exposure of portions of the film according to the level of radiation present in the surface layers at that location on the object's surface adjacent the film. The activation does not need to be homogeneous, and the autoradiography may vary in visual density when optically scanned and digitized.

The object is then worn during testing or during routine operation. This process removes some of the surface material, and thereby reduces the radioactivity where the wear occurs most. In the case of an engine cylinder for example, the common worn regions are at the piston ring motion reversal positions due to the reciprocating action. A second autoradiograph is then taken from the worn object and likewise digitized. This second autoradiograph is then compared with the first and a subtraction methodology is used to highlight the differences. This approach can thereby reveal the areas that have changed due to wear-induced reductions in radioactivity. This results in a direct optical mapping of the wear that has occurred. Sensitivity is based primarily on the depth and uniformity of surface activation. Various methods for addressing non-linear film response, natural (non-wear induced) radioactive decay, and other film based non-homogeneities may be applied to improve quantitative results.

Digital image processing makes it possible to obtain before and after contact autoradiographs of a radioactive wear surface in order to create three-dimensional maps of wear by subtractive image intensity. This approach can be particularly useful when the surface layer activation (SLA) is well characterized with respect to the depth distribution of a radioactive species, and SLA calibration coupons are available to allow accurate quantification of the radiation levels. Such surface layer activation methods are routinely used in wearing components like engine cylinder bores. The resultant wear maps are functionally equivalent to three-dimensional profile metrics and can be obtained with far less effort and expense when the activations are carried out for other aspects of wear investigation. Therefore, autoradiography based wear mapping can provide added value when used in conjunction with routine radioactive tracer technology. Autoradiography based wear mapping may also be justifiable in many cases as the primary investigatory method.

BRIEF DESCRIPTION OF THE DRAWINGS

FIG. 3A provides an example of what a typical post-wear autoradiography image rendered on photographic or x-ray film in two-dimensional format might look like.

DETAILED DESCRIPTION OF THE PREFERRED EMBODIMENTS

Figure 1:
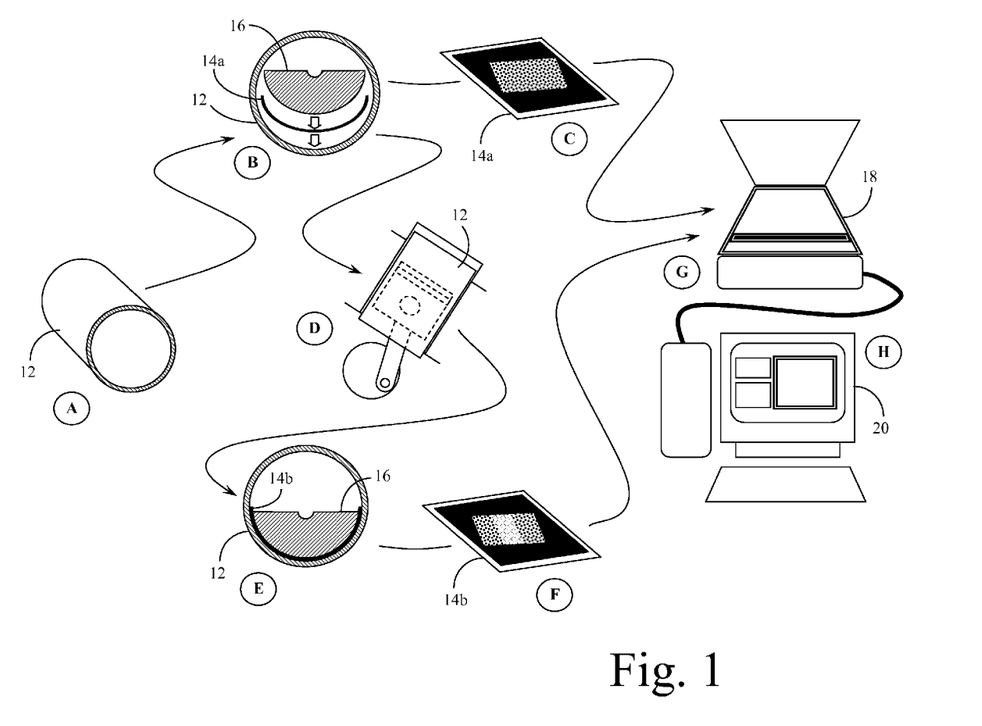
FIG. 1 provides a schematic diagram showing the overall system and method of a preferred implementation of the present invention.

As indicated above, the method and system of the present invention provide a means for characterizing, tracking, and monitoring the level of wear experienced by an object's surface, typically some object that experiences repetitive motion either of itself or from another object moving against it, such as with an engine cylinder wall and the associated moving piston (with piston rings). FIG. 1 provides a schematic diagram showing the overall system and method of a preferred implementation of the present invention, as used in an example with an engine cylinder wall liner. The various steps in the method, generally identified in FIG. 1, are described in more detail below with respect to the flowchart shown in FIG. 5.

The first step in the process, shown as Step A in FIG. 1, involves activating a surface layer of an object 12 such as an engine cylinder liner or the like. This surface layer activation may be carried out over some or all of the wearing surface of the object 12. This surface layer activation produces radioactive elements in the first several microns of the surface to be studied. A first reference autoradiograph is then taken, shown as Step B in FIG. 1, by placing a conformal photographic or x-ray film 14a in direct contact with the activated surface on the object 12 and thereby exposing the film 14a to radioactive emissions from the surface of the object 12 for some defined period of time. A shaped form 16 may be used to facilitate the positioning and placement of the conformal photographic of x-ray film 14a against the wearing surface.

The photographic or x-ray film 14a is then developed, at Step C in FIG. 1, to provide an autoradiograph image which in turn provides a baseline map of the radioactivity present in the surface of the object 12 according to the indexed positioning of the photographic or x-ray film 14a. As indicated above, the activation does not need to be homogeneous as for the most part it is a comparison that is being made rather than a reference to some definitive level. The autoradiograph may in fact vary in visual density when optically scanned and digitized even if no wearing has yet occurred on the surface of the object.

Step D in FIG. 1 shows the process of wearing the surface of the object 12 within a machine assembly or the like. This wearing could occur during testing or could simply involve the monitoring of an object's surface during normal use. After a period of time the object 12 is removed from the mechanical system and a second autoradiograph is obtained, as shown in Step E of FIG. 1. This "post wear" autoradiograph 14b, after being developed as shown in Step F of FIG. 1, will exhibit the signs of wear on the surface of the object 12 by changes in the image on the autoradiograph. Typically, these changes will take the form of variations in image intensity (brightness) resulting from the decreased level of radiation in those portions of the activated surface that have worn away. The pattern of this wearing will therefore be visible in the autoradiographic image.

Although some information about the character of the wearing surface might be obtained from a visual comparison between the two acquired autoradiographs, quantifying this information with only visual inspection can be difficult. The final steps in the process of the present invention, shown generally as Step G and Step H in FIG. 1, involve scanning and digitizing the autoradiographic images and processing this digital data to compile three-dimensional graphic representations of the objects surface, both before and after wearing occurs. The image information, once digitized may be used to construct differential graphic representations that further high-light the manner in which the surface is being worn. These steps may be carried out using any of a number of image scanning devices 18 in conjunction with digital computer processors 20 to establish data of appropriate resolution to allow for the data processing, analysis, and graphic displays required by the present invention.

Figure 2A:
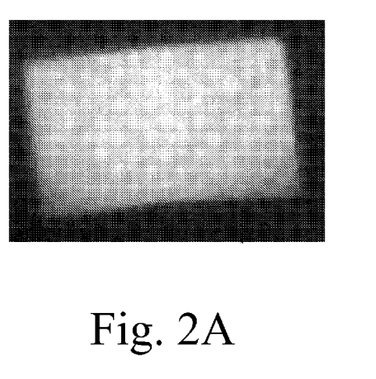
FIG. 2A provides an example of a base line autoradiography image rendered on photographic or x-ray film in two-dimensional format.

FIG. 2A provides an example of a base line autoradiography image rendered on photographic or x-ray film in two-dimensional format. In this view, some variations in the image intensity (brightness) represent the permissible non-homogenous distribution of radiation as a result of the activation of the surface layers of the object. As indicated above, these variations are not critical as it is a comparison with this base line image that provides the relevant wear data for analysis and wear characterization.

Figure 2B:
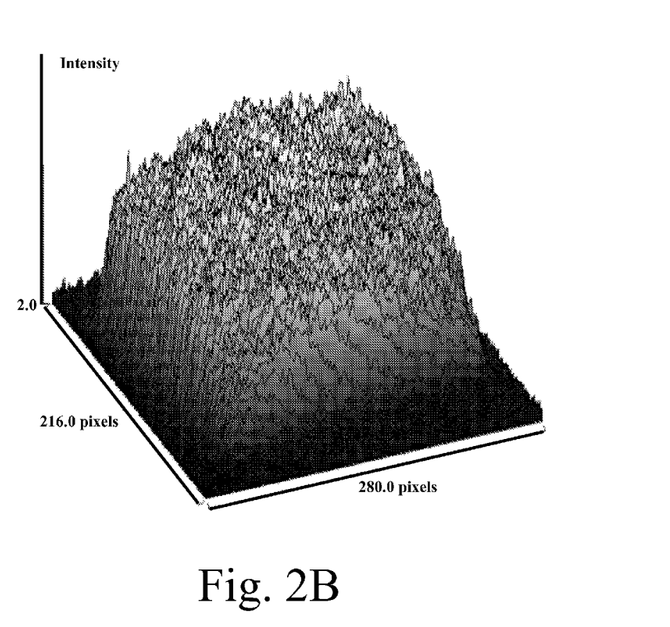
FIG. 2B is a three-dimensional representation of digitized data taken from the autoradiography image shown in FIG. 2A.

FIG. 2B is a three-dimensional representation of digitized data taken from the autoradiography image shown in FIG. 2A. A precise method of physical indexing is used in this initial base line imaging process to allow subsequent autoradiographs to be produced with identical positioning and mapping. This indexing may be a combination of accurately positioning the film (itself of a fixed geometry) physically on the object using reference structures and/or using non-variable image references that are displayed on the resultant autoradiographs. The type of indexing will be dependent on the structure being studied and the availability of physical reference points or image reference features.

In FIG. 2A a two-dimensional image of the object under study is provided within which greater intensities of radiation show up as brighter portions of the two-dimensional image. A three-dimensional image lends a quantitative value to the digitized readings associated with the level of radioactivity over the two-dimensional surface area of the object. In FIG. 2B, therefore, the darker (and lower) digital quantities shown on the three-dimensional graph indicate low levels of radiation experienced over the period of time that the photographic image was exposed. The higher peaks, which generally are represented by brighter components in the graph, indicate areas where the level of radiation is still quite high.

As described above, once the reference base line image has been established, the object is placed into service, or into a testing environment, where the procedures it undergoes cause wear to the surface under investigation. Typically the constant motion associated with the surface of the object removes some of the surface material and thus reduces the radioactivity specifically where the greatest wear occurs. If in the case of an engine cylinder liner, for example, the common worn regions are at the piston ring motion reversal positions, one would expect that discreet areas of wear can be discerned from significant reductions in the level of radiation from those areas.

Figure 3A:
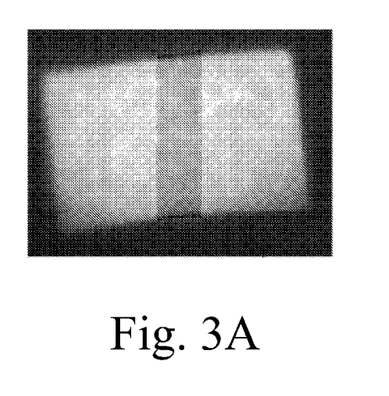
Figure 3B:
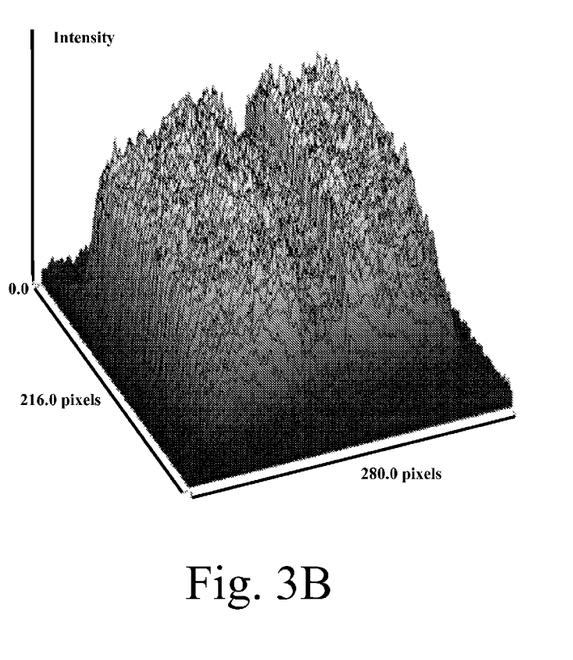
FIG. 3B is a three-dimensional representation of digitized data taken from the sample autoradiography image shown in FIG. 3A.
Figure 4:
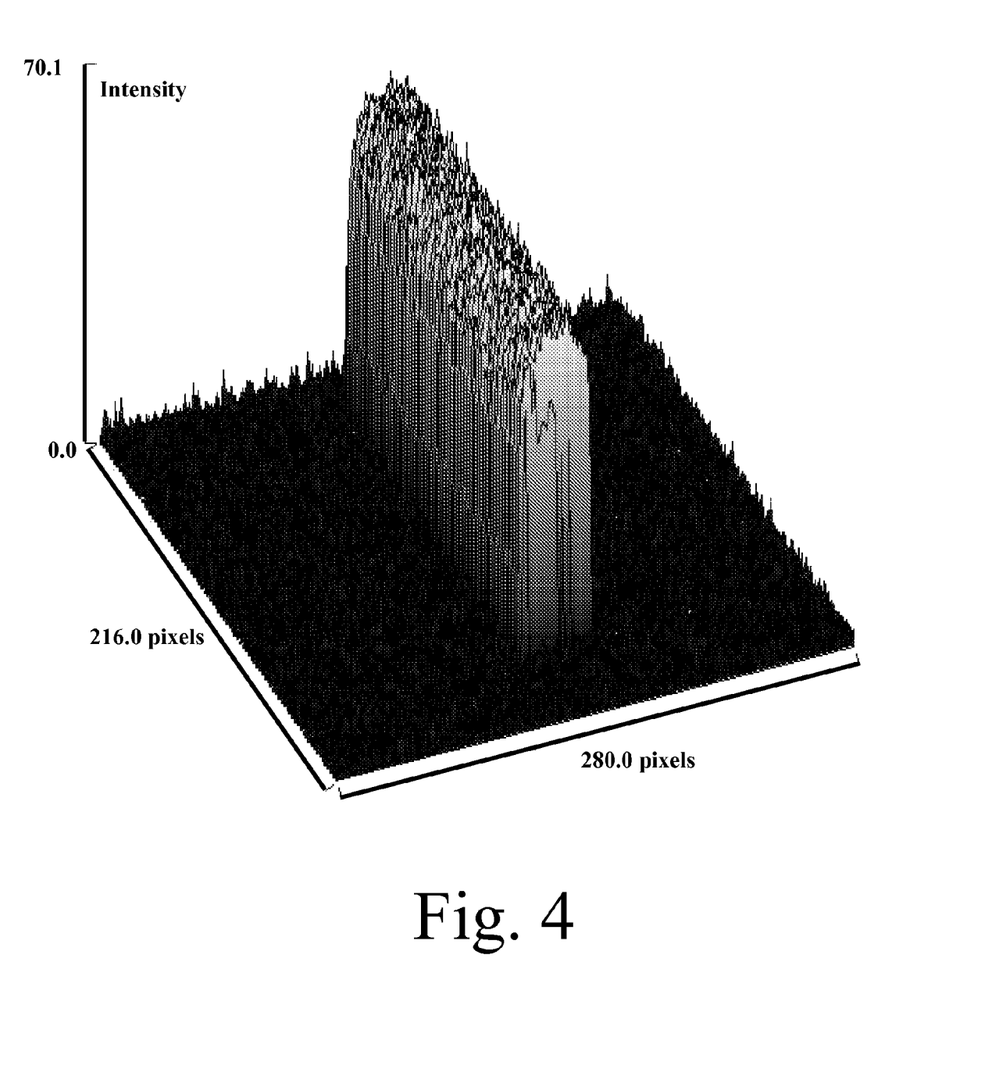
FIG. 4 is a three-dimensional representation of a wear scar map created by subtraction of the data shown in FIG. 3B from the data shown in FIG. 2B.

After a significant amount of wear has occurred, a second autoradiograph is taken from the object and is digitized to create a graphic representation similar to that shown in FIGS. 3A & 3B. FIG. 3A shows an example of what an autoradiographic image might look like following testing that has produced a wear scar in a particular region of the material. FIG. 3B is a three-dimensional representation of digitized data taken from the autoradiography image shown in FIG. 3A. This autoradiograph is then computationally brought into registry and compared with the first baseline autoradiograph. This comparison takes the form primarily of a subtraction methodology that is used to highlight the differences that are disclosed. This highlight or subtraction methodology results in the graphic that is shown in FIG. 4. Such a method approach provides a high contrast characterization of the areas that have changed due to the wear-induced reductions in radioactivity.

FIG. 4 is a three-dimensional representation of a relatively simple wear scar map created by subtraction of the data shown in FIG. 3B from the data shown in FIG. 2B wherein, for example, a single band of relatively consistent wearing might have occurred on the surface. The methods and system of the present invention are quite capable, however, of characterizing much more complex wear patterns on a variety of surfaces with varying geometries. The three-dimensional graphics shown in FIG. 2B, FIG. 3B and FIG. 4, may of course be rotated and zoomed (within the processor/display system) to isolate and highlight any specific region of interest in the data. In this manner very fine variations in the wear patterns may be discerned.

The comparison between the pre-wear and post-wear autoradiographs (and their digital representations) can be made by an individual visually comparing the two images created, or can be accomplished in automated fashion by identification of the appropriate characteristics of the surface wear. The result, as indicated above, is a direct optical mapping of the wear that has occurred on the surface area under investigation. The sensitivity of the method can be varied, and is based on the depth of the surface activation which affects the proportion of the radioactive material removed during a wear event. Shallow activations, for example, produce higher contrast after the surface is worn. That is, the method can be made extremely sensitive to slight wear if so desired. Variations in the level of surface level activation can therefore be chosen depending upon the circumstances and the anticipated wear to be experienced. While shallow activations may produce higher contrasts under limited wear conditions, they also lose their effectiveness when excessive wear occurs and most if not all of the surface level activation is worn away. Deeper activation may therefore be called for when significant wear is expected, at least in certain areas of the object under examination.

It should be noted at this point that the film response to radiation intensity is not necessarily linear. Therefore, in order to make quantitative, and in many cases even qualitative radiation intensity maps, the film response needs to be characterized and a transfer function applied to the scanned image data to correct for non-linearity. There are at least three methods that can be used to map the film response function. A specific film response to radiation intensity can be characterized or calibrated through: (a) a series of incremental length time exposures on a single activated surface of the same isotope; (b) a series of exposures to a number of surfaces of the same isotope with varying, known levels of induced radioactivity; and/or (c) a series of repeated same time length exposures to a single surface of the same isotope over time to allow for time decay of surface activity.

Once the film response is mapped, a transfer function can be mathematically derived and used to normalize the digitized images. Once normalized and barring non-homogeneities in the film, subtraction of before and after wear images will produce a qualitative map of the wear scar. This resulting image can then also be used to produce a quantitative 3-dimensional wear scar map.

In addition to accounting for film non-linearity, the image intensity of the post-wear scar will over time be affected by natural radioactive decay. Radioactive materials decay at a fixed, known rate. Even without wear induced removal of radioactive material, the rate of radioactive emissions from the activated surface will change uniformly over time. A correction to radioactive intensity can be made mathematically by applying Equation 1 set forth below:

$$\text{Corrected Intensity} = \text{Measured Intensity} * \exp(0.693 * \text{Decay-Time/Half-life}) \quad [\text{Eq. 1}]$$

Since film response may not necessarily be linear with radiation intensity, this decay correction equation may not be sufficient to correct for resulting image intensity. The above equation must therefore be combined with the previously described film response transfer function in order to correct for natural radioactive decay.

A further method of correcting for natural decay is to activate an area on the surface of the test article that is known not to experience wear. This area should be adjacent to or at least proximally near the known wear area to facilitate simultaneous exposure of the non-worn and worn areas on the same film. By comparing the resulting non-worn and worn exposures, a correction can be made to the autoradiograph image to account for time derived decay. The film response transfer function described above would be utilized to reference these measurements before comparison.

In general, the above described quantitative characterization of the film response allows the use of correction factors to compensate for both natural isotopic decay and response non-linearity between the time of taking baseline measurements and the time of taking post-test (post-wear) exposures. Those skilled in the art will recognize that additional algorithms may be needed to correct for any film or image background non-homogeneities in order to generate a more accurate quantitative three-dimensional mapping of the resulting wear scar.

Figure 5:
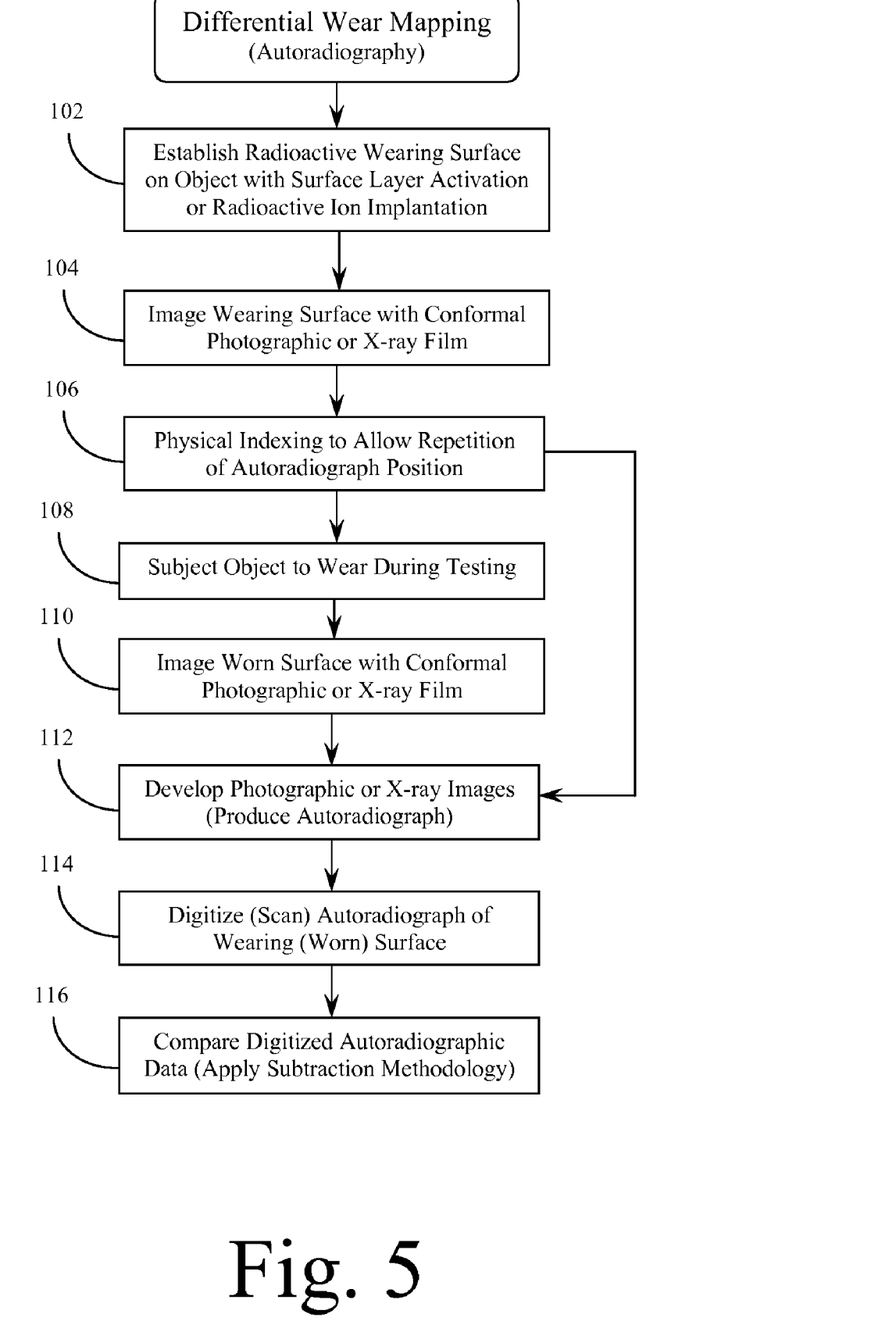
FIG. 5 is a flowchart showing the basic steps in the implementation of a preferred embodiment of the method of the present invention.

Reference is finally made to FIG. 5 for a description of a flowchart showing the basic steps in the implementation of a preferred embodiment of the method of the present invention. This Differential Wear Mapping methodology begins with the establishment of a radioactive wearing surface on the object to be studied as described in Step 102 in FIG. 5. In the preferred embodiment this is accomplished either through surface layer activation (SLA) or radioactive ion implantation (RII) to establish radioactive material within the surface layer levels of the object. SLA can be carried out by any of a number of known techniques ranging from a simple timed exposure to fissioning radioactive material to targeting the surface with an accelerated particle beam to implanting energetic radioactive ions within the surface layers. The objective is simply to establish a level of radioactivity in the surface layers of the object that will be maintained relatively constant for the period of time during which wear testing is to occur. In Step 104, conformal photographic or x-ray film is positioned against the wearing surface so as to create a baseline image of the radiation distribution. An important component of the imaging process (both pre-wear and post-wear) is described in Step 106 with the process of physical indexing of the film to allow for accurate repetition of the autoradiography. As indicated above, this indexing may be one or a combination of physical geometric indexing and/or image landmark referencing.

The object under study is then subjected to wear at Step 108, during testing or during normal use in a mechanical system. After a period of time determined by the specific circumstances of the system, the object is removed from the mechanical wear system for the creation of a second autoradiograph. At Step 110 the worn surface is imaged in much the same manner (and according to the same indexing process) as the initial base line image. Step 112 describes the process of developing the photographic or x-ray film to produce the before and after autoradiographs. It is understood that these need not be simultaneously developed and that initial creation of the visual (and perhaps digitized) base line autoradiograph may occur prior to subjecting the object to wear during testing. In any event, the films representing the autoradiographs are developed at Step 112 and then digitized at Step 114. The process at Step 114 of digitizing the images will typically take the form of scanning the autoradiographs and coordinating two dimensional data points identifying a position on the object's surface, with an intensity data point representative of the level of radiation at that position. In this manner, three-dimensional graphic representations of the wearing surface and the radiation levels can be generated.

Finally, at Step 116, a comparison methodology is implemented that compares the data associated with the base line autoradiograph and the subsequently acquired post-wear autoradiograph(s). In the preferred embodiment this comparison methodology comprises a subtraction method that results in a differential wear map that provides strong contrast between the areas of the surface that experienced significant wear and those that did not. In some cases this differential map might represent a negative (or positive) representation of the geometry of the surface after wear although such a result is not an essential step in the method of the present invention. Significant information can be obtained from mapping the wear patterns even if the map is not a true representation of the post-wear physical appearance of the surface.

While the above-described method is inherently differential in nature (i.e. a comparison is carried out between a reference value and a subsequently measured value) it can also be made quantitative if radioactive reference coupons are placed against the film to permit calibrated exposures. This will allow a densitometry based quantitative measurement of the actual depth of wear if the depth distribution of the radioactive species is known.

In the manner described, the present invention therefore provides systems and methods for measuring the wear on a surface utilizing contact autoradiographs of residual radiation established by surface layer activation and comparing (subtracting) data derived from these autoradiographs to construct a map of the surface wear patterns. The resultant differential wear maps provide valuable information on both the causes of wear and the rate at which different portions of the surface experience wear.

In addition to measuring wear, the systems and methods of the present invention may be similarly used to track the displacement of material on a surface (such as a sealant or the like), or to map the transfer of material from one surface to another.

Although the present invention has been described in terms of the foregoing preferred embodiments, this description has been provided by way of explanation only, and is not intended to be construed as a limitation of the invention. Those skilled in the art will recognize modifications of the present invention that might accommodate specific wear testing and monitoring environments and structures. Those skilled in the art will further recognize additional methods for compensating for non-linearities and other non-homogeneities in the film and the radioactive activation. Such modifications, as to structure, orientation, geometry, and even radiation activation and detection techniques, where such modifications are coincidental to the type of testing or monitoring environment present, do not necessarily depart from the spirit and scope of the invention.

We claim:

1. A system for differential wear mapping of the surface of an object, the system comprising:
   (a) a device for establishing a radioactive wearing surface on the object;
   (b) a first conformal radiation imaging device for producing a first autoradiograph providing a baseline profile of the wearing surface;
   (c) a second conformal radiation imaging device for producing a second autoradiograph providing a worn profile of the wearing surface;
   (d) a digitizer for establishing first and second data sets representing the first and second autoradiographs; and
   (e) a data processor for comparing the first and second data sets and establishing a differential data set, the differential data set characterizing a differential wear map of the surface of the object.

2. The system of claim 1 wherein the device for establishing a radioactive wearing surface comprises a device for surface layer activation (SLA) of the surface layers of the object.

3. The system of claim 1 wherein the device for establishing a radioactive wearing surface comprises a device for radioactive ion implantation (RII) in the surface layers of the object.

4. The system of claim 1 wherein the first and second conformal radiation imaging devices each comprise a sheet of flexible photographic imaging film.

5. The system of claim 1 wherein the first and second conformal radiation imaging devices each comprise a sheet of flexible x-ray imaging film.

6. The system of claim 1 wherein the first and second conformal radiation imaging devices each comprise a conformable two-dimensional solid state detector array.

7. The system of claim 4 wherein the digitizer comprises an image scanner for creating digital image data of the sheet of flexible photographic imaging film.

8. The system of claim 5 wherein the digitizer comprises an image scanner for creating digital image data of the sheet of flexible x-ray imaging film.

9. The system of claim 6 wherein the digitizer comprises a digital image processor for creating digital image data from the output of the solid state detector array.

10. The system of claim 1 further comprising an indexing device for consistent positioning and repositioning of the first and second conformal radiation imaging devices on the wearing surface of the object.

11. A system for differential wear mapping of the surface of an object, the system comprising:
   (a) a surface layer activation/implantation device for establishing a radioactive wearing surface on the object;
   (b) a first sheet of flexible radiation imaging film conformable to the surface of the object for producing a first autoradiograph providing a baseline profile of the wearing surface;
   (c) a second sheet of flexible radiation imaging film conformable to the surface of the object for producing a second autoradiograph providing a worn profile of the wearing surface;
   (d) an indexing device for consistent positioning and repositioning of the first and second sheets of flexible radiation imaging film on the wearing surface of the object;
   (e) a digital scanner for establishing first and second digital data sets representing the first and second autoradiographs; and
   (f) a data processor for comparing the first and second data sets and establishing a differential data set, the differential data set characterizing a differential wear map of the surface of the object.

12. A method for differential wear mapping of the surface of an object, the method comprising the steps of:
   (a) establishing a radioactive wearing surface on the object;
   (b) imaging the wearing surface to produce a first autoradiograph providing a baseline profile of the wearing surface;
   (c) subjecting the object to wear during testing;
   (d) imaging the wearing surface to produce a second autoradiograph providing a worn profile of the wearing surface;
   (e) digitizing the first and second autoradiographs of the wearing surface; and
   (f) comparing the digitized first and second autoradiograph to produce a differential wear map of the surface of the object.

13. The method of claim 12 wherein the step of establishing a radioactive wearing surface on the object comprises carrying out a surface layer activation (SLA) process on the surface layers of the object.

14. The method of claim 12 wherein the step of establishing a radioactive wearing surface on the object comprises carrying out a radioactive ion implantation (RII) process in the surface layers of the object.

15. The method of claim 12 wherein each of the steps of imaging the wearing surface comprise positioning, conforming, and exposing a sheet of flexible photographic imaging film to the wearing surface of the object.

16. The method of claim 12 wherein each of the steps of imaging the wearing surface comprise positioning, conforming, and exposing a sheet of flexible x-ray imaging film to the wearing surface of the object.

17. The method of claim 12 wherein each of the steps of imaging the wearing surface comprise positioning, conforming, and exposing a two-dimensional solid state detector array to the wearing surface of the object.

18. The method of claim 12 further comprising the step of indexing a position of the first autoradiograph so as to allow repetition of the step of imaging the wearing surface.

19. The method of claim 12 further comprising the step of compensating for any non-linear response characteristics in the wearing surface imaging steps, for any non-wear induced reductions in radiation, and for any non-homogeneity in the imaging medium.

20. A method for differential wear mapping of the surface of an object, the method comprising the steps of:
   (a) establishing a radioactive wearing surface on the object through surface layer activation (SLA) or radioactive ion implantation (RII);
   (b) imaging the wearing surface with conformal photographic/x-ray film to produce a first autoradiograph providing a baseline profile of the wearing surface;
   (c) indexing a position of the first autoradiograph so as to allow repetition of the step imaging the wearing surface;
   (d) subjecting the object to wear during testing;
   (e) imaging the wearing surface with conformal photographic/x-ray film to produce a second autoradiograph providing a worn profile of the wearing surface;
   (f) digitizing the first and second autoradiographs of the wearing surface;
   (g) compensating for any non-linear response characteristics of the photographic/x-ray film, for any non-wear induced reductions in radiation, and for any non-homogeneity in the photographic/x-ray film; and
   (h) comparing the digitized first and second autoradiograph to produce a differential wear map of the surface of the object.

* * * * *